US006447819B2

(12) United States Patent
Paracchini

(10) Patent No.: US 6,447,819 B2
(45) Date of Patent: Sep. 10, 2002

(54) WATER-SOLUBLE COMPLEX OF AN EXTRACT OF *GINKGO BILOBA*, PROCESS FOR THE PREPARATION THEREOF AND COMPOSITION COMPRISING THE SAME

(75) Inventor: Silvano Paracchini, Muralto (CH)

(73) Assignee: Linnea SA, Riazzino (CH)

( * ) Notice: Subject to any disclaimer, the term of this patent is extended or adjusted under 35 U.S.C. 154(b) by 0 days.

(21) Appl. No.: 09/853,695

(22) Filed: May 14, 2001

(30) Foreign Application Priority Data

Jun. 16, 2000 (EP) .............................. 00202088

(51) Int. Cl.$^7$ .............................. A01N 65/00
(52) U.S. Cl. ...................................... 424/752
(58) Field of Search .......................... 424/752

(56) References Cited

U.S. PATENT DOCUMENTS 6,258,840 B1 * 7/2001 Golding et al. ............. 514/457

FOREIGN PATENT DOCUMENTS

| FR | 2 755 015 | 4/1998 |
| WO | WO 00/01397 | 1/2000 |

OTHER PUBLICATIONS

Drieu, "Preparation and Definition of Ginko Biloba," La Presse Medicale, Sep. 25, 1986, vol. 15, No. 31, pp. 1445–1457.

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

A water-soluble complex of N-methylglucamine with an extract of Ginkgo biloba leaves, process for the preparation thereof and composition comprising the same.

5 Claims, No Drawings

WATER-SOLUBLE COMPLEX OF AN EXTRACT OF GINKGO BILOBA, PROCESS FOR THE PREPARATION THEREOF AND COMPOSITION COMPRISING THE SAME

This application is based on European Patent Application No. 00202088.1 filed on Jun. 16, 2000, the content of which is incorporated hereinto by reference.

The present invention relates to a water-soluble complex of an extract of *Ginkgo biloba,* to a process for the preparation thereof and to a composition comprising the same.

More particularly, the present invention relates to a water-soluble complex of an extract of *Ginkgo biloba* with N-methylglucamine.

It is known that the leaves of *Ginkgo biloba* contain a host of heterogeneous substances formed of both liposoluble and water-soluble compounds.

Extracts of *Ginkgo biloba* have been studied for years both from a chemical point of view and from a pharmacological and clinical point of view since they comprise compounds endowed with cerebral and peripheral vasomotor activity.

In approximate terms, the dry extracts used in pharmaceuticals have the following composition:
- about 24% w/w of heterosides (expressed as flavone glycosides, consisting mainly of quercetin-3-O-(6'''-trans-p-cumaroyl-2''-glucosyl)rhamnoside and kaempferol and isorhamnetin-3-O-(6'''-trans-p-cumaroyl-2''-glucosyl)rhamnoside);
- about 6% w/w of bilobalide and ginkgolides J, A, B and C;
- about 3–4% w/w of proanthocyanidins (consisting of mixtures of anthocyanidins and delphinidin dimers and polymers);

the balance consisting of not yet clearly identified inert plant matter.

However, the abovementioned extracts are not soluble in water.

To overcome this drawback, patent application WO 00/01397 discloses a water-soluble dry extract obtained from an hydroalcoholic extract of *Ginkgo biloba* leaves by means of targeted ultrafiltration.

Patent application FR-A-2 755 015 discloses an extract of flavonoids from *Ginkgo biloba* leaves, with a low content of other components, which has anti-elastase and anti-inflammatory activity on human gums. The said document also describes a pharmaceutical composition containing the abovementioned extract for the topical treatment of the abovementioned complaints. The pharmaceutical compositions can also be in liquid form. However, the document never mentions aqueous solutions since the abovementioned extract is not water-soluble.

Thus, there is still a great need for an extract of *Ginkgo biloba* leaves which is particularly rich in flavonoids and which has a low content of other components, and which is also water-soluble.

In the present description and in the claims, the term "water-soluble" means a solubility in water of at least 1% (w/v).

It has now been found, surprisingly, that this aim can be achieved by forming a complex of an extract of *Ginkgo biloba* with N-methylglucamine. Indeed, it was entirely unpredictable that N-methylglucamine would interact with many of the components of the abovementioned extract which lack an acid function.

It is therefore a first object of the present invention to provide a water-soluble complex of N-methylglucamine with an extract of *Ginkgo biloba* leaves.

Furthermore, it is a second object of the present invention to provide a process for preparing a water-soluble complex of an extract of *Ginkgo biloba* leaves with N-methylglucamine, the said process comprising the steps of:
a) adding N-methylglucamine to an alcoholic solution of the said extract,
b) filtering the solid product obtained from step a), and
c) removing the solvent.

The composition of the extract of *Ginkgo biloba* leaves reacted with N-methylglucamine is preferably as follows:
- flavone glycosides: 22–45% (w/w),
- ginkgolides 0.1–12% (w/w),
- bilobalide: 0.01–5% (w/w),
- proanthocyanidins: 3–8% (w/w).

The amount of extract reacted on a dry-weight basis is preferably of about 1.5–3.0 times and even more preferably to twice the weight of the N-methylglucamine.

The said alcoholic solution is typically a solution of a saturated aliphatic alcohol having of from 1 to 4 carbon atoms and having a linear or branched chain, such as, for example, methanol, ethanol or isobutanol.

Preferably, step a) is carried out at a temperature of between 0°C and the boiling point of the reaction mixture. Even more preferably, this temperature is between 20 and 70° C.

Step c) is typically carried out by evaporating off the solvent under reduced pressure.

The composition of the thus obtained water-soluble complex is advantageously as follows:
- flavone glycosides: 15–30% (w/w),
- ginkgolides: 0.1–7% (w/w),
- bilobalide: 0–2% (w/w),
- proanthocyanidins: 1–2% (w/w)
- N-methylglucamine: 32–34% (w/w),
- water-soluble inert plant matter: 25–51.9% (w/w).

Finally, it is a third object of the present invention to provide a composition comprising a water-soluble complex of N-methylglucamine with an extract of *Ginkgo biloba* leaves, characterized in that the said complex is rich in flavonoids and has a low content of other components.

The said complex typically has a water solubility of between 1 and 30% (w/v), and even more typically the said solubility is of from 3 to 10% (w/v).

The examples which follow intend to illustrate the present invention without, however, limiting it in any way.

EXAMPLE 1

Preparation of the Starting Extracts

The extracts of *Ginkgo biloba* leaves used in Examples 2 to 7 had the compositions indicated in Table 1 and were prepared as follows:

a) Extracts 564, 597 and 564a

Dried *Ginkgo biloba* leaves were extracted with aqueous 60% acetone at 50–60° C. The thus obtained solution was concentrated to give an aqueous paste, which was cooled and filtered. Butanol was added to the thus obtained paste and the organic phase was separated out and concentrated under vacuum to an aqueous residue. The aqueous residue was washed with heptane and the alkane phase was removed. The aqueous phase was treated with ethanol, filtered and finally concentrated to dryness. The dry residue was then dried to constant weight in a vacuum oven. The obtained solid product was reduced to a fine powder.

The various compositions of the thus obtained extracts (Table 1) reflect the diverse content of the various components in the starting leaves.

b) Extract 633

The process was performed as in the above case, except that the aqueous residue, obtained after removing the butanol, was extracted with ethyl acetate. The organic phase, containing ginkgolides and bilobalides, was removed, while the resulting aqueous phase was treated as described above.

c) Extracts 632 and 640

These were prepared from extract 633, which has a low content of terpenes, by means of the extemporaneous addition of a fraction enriched in ginkgolides J, A, B and C which was prepared by purifying the ethyl acetate solution removed in the process for preparing the de-terpenated extract 633.

TABLE 1

| Extract No | Flavone glycosides % (w/w) | Ginkgolides % (w/w) | Bilobalide % (w/w) | Proanthocyanidins % (w/w) |
|---|---|---|---|---|
| 564 | 28.03 | 4.06 | 3.37 | 4.64 |
| 597 | 27.15 | 7.25 | 3.26 | 4.44 |
| 564a | 28.03 | 4.06 | 3.37 | 4.64 |
| 632 | 38.17 | 4.3 | 0.28 | 3.22 |
| 633 | 41.22 | 0.5 | 0.1 | 3.48 |
| 640 | 36.15 | 8.94 | 0.1 | 3.04 |

EXAMPLE 2

Preparation of the N-methylglucamine/extract Complex (Weight Ratio 1:2)

A solution of extract 564 (20 g) of Table I in methanol (200 ml) was placed in a reactor equipped with a reflux condenser and a stirrer. The mixture was kept stirring until the solid extract had fully dissolved. This solution was then heated to 60° C. and N-methylglucamine (10 g) was added thereto. The mixture was maintained at reflux for 15 minutes with stirring, cooled to 30° C. and filtered. The thus obtained solution was concentrated under reduced pressure and at a temperature of not more than 50° C. The resulting solid residue was ground and brought to dryness under reduced pressure and at a temperature of not more than 70° C.

26.74 g of the desired product were thus obtained (yield= 89%).

The analysis of the said product gave the results illustrated in Tables 2 and 3 below.

TABLE 2

| Colour: | Brown-yellow |
|---|---|
| Solubility in distilled water: | 10% |
| pH (c = 1% in water): | 7.84 |

TABLE 3

| Compounds | Found (%) | Expected (%) |
|---|---|---|
| Flavone glycosides | 18.9 | 18.69 |
| Ginkgolides | 2.7 | 2.72 |
| Bilobalide | 0.38 | 2.24 |
| Proanthocyanidins | 1.7 | 3.09 |
| N-methylglucamine | 32.6 | 33.3 |

EXAMPLE 3

Preparation of the N-methylglucamine/extract Complex (Weight Ratio 1:2.25)

The process was performed in a manner similar to that described in Example 2 above, except that extract 597 (10.42 g) of Table 1 was used and the amount of N-methylglucamine was 4.63 g.

13.5 g of the desired product were thus obtained (yield= 90%).

The analysis of the said product gave the results indicated in Tables 4 and 5.

TABLE 4

| Colour: | Brown-yellow |
|---|---|
| Solubility in distilled water: | 10% |
| pH (c = 1% in water): | 7.5 |

TABLE 5

| Compounds | Found (%) | Expected (%) |
|---|---|---|
| Flavone glycosides | 18.9 | 18.85 |
| Ginkgolides | 4.41 | 5.02 |
| Bilobalide | 0.54 | 2.26 |
| Proanthocyanidins | 1.61 | 3.07 |
| N-methylglucamine | 31.3 | 30.8 |

EXAMPLE 4

Preparation of the N-methylglucamine/extract Complex (Ratio 1:2.3)

A solution of extract 564a (10 g) of Table 1 in methanol (90 ml) was placed in a reactor equipped with a reflux condenser and a stirrer. The mixture was kept stirring at room temperature until the solid extract had fully dissolved. N-methylglucamine (4.35 g) dissolved in water (10 ml) was added to the solution. The mixture was stirred for 5 minutes and filtered. The thus obtained solution was concentrated under reduced pressure and at a temperature of not more than 50° C. The resulting solid residue was ground and brought to dryness under reduced pressure and at a temperature of not more than 70° C.

13.22 g of the desired product were thus obtained (yield= 92%).

The analysis of the said product gave the results shown in Tables 6 and 7.

TABLE 6

| Colour: | Brown-yellow |
|---|---|
| Solubility in distilled water: | 10% |
| pH (c = 1% in water): | 9.58 |

TABLE 7

| Compounds | Found (%) | Expected (%) |
|---|---|---|
| Flavone glycosides | 17.1 | 19.7 |
| Ginkgolides | 2.9 | 2.9 |
| Bilobalide | 1.3 | 2.4 |
| Proanthocyanidins | 1.78 | 3.23 |
| N-methylglucamine | 30.0 | 30.3 |

EXAMPLE 5

Preparation of the N-methylglucamine/extract Complex (Ratio 1:2)

The process was performed in a manner similar to that described in Example 4 above, except that extract 632 (54 g)

of Table 1 in 849 ml of methanol was used and the amount of N-methylglucamine added was 28 g.

77 g of the desired product were thus obtained (yield=94%). The analysis of the said product gave the results shown in Tables 8 and 9.

TABLE 8

| Colour: | Brown-yellow |
|---|---|
| Solubility in distilled water: | 1% |
| pH (c = 1% in water): | 7.8 |

TABLE 9

| Compounds | Found (%) | Expected (%) |
|---|---|---|
| Flavone glycosides | 22.3 | 25.7 |
| Ginkgolides | 4.13 | 4.15 |
| Bilobalide | 0.1 | 0.15 |
| Proanthocyanidins | 1.27 | 2.12 |
| N-methylglucamine | 33.7 | 33.3 |

EXAMPLE 6

Preparation of the N-methylglucamine/extract Complex (Ratio 1:2)

The process was performed in a manner similar to that described in Example 4 above, except that extract 633 (10 g) of Table 1 in 150 ml of methanol was used and the amount of N-methylglucamine added was 5 g.

13 g of the desired product were thus obtained (yield=86%).

The analysis of the said product gave the results shown in Tables 10 and 11.

TABLE 10

| Colour: | Brown-yellow |
|---|---|
| Solubility in distilled water: | 30% |
| pH (c = 1% in water): | 7.8 |

TABLE 11

| Compounds | Found (%) | Expected (%) |
|---|---|---|
| Flavone glycosides | 27 | 27 |
| Ginkgolides | 0.3 | 0.3 |
| Bilobalide | 0 | 0.06 |
| Proanthocyanidins | 1.2 | 2.32 |
| N-methylglucamine | 33.2 | 33.3 |

EXAMPLE 7

Preparation of the N-methylglucamine/extract Complex (Ratio 1:2)

The process was performed in a manner similar to that described in Example 2 above, except that extract 640 (91.23 g) of Table 1 in 1370 ml of methanol was used and the amount of N-methylglucamine added was 45.61 g.

123.2 g of the desired product were thus obtained (yield=90%).

The analysis of the said product gave the results shown in Tables 12 and 13.

TABLE 12

| Colour: | Brown-yellow |
|---|---|
| Solubility in distilled water: | 1% |
| pH (c = 1% in water): | 8.0 |

TABLE 13

| Compounds | Found (%) | Expected (%) |
|---|---|---|
| Flavone glycosides | 22.9 | 24.1 |
| Ginkgolides | 5.96 | 6.0 |
| Bilobalide | 0.17 | 0.1 |
| Proanthocyanidins | 1.00 | 2.03 |
| N-methylglucamine | 33.2 | 33.3 |

What is claimed is:

1. A water-soluble complex of N-methylglucamine with an extract of *Ginkgo biloba* leaves, said extract comprising flavone glycosides and ginkgolides as components.

2. A complex according to claim 1, characterized in that it has the following composition:
   flavone glycosides: 15–30% (w/w),
   ginkgolides: 0.1–7% (w/w),
   bilobalide: 0–2% (w/w),
   proanthocyanidins: 1–2% (w/w)
   N-methylglucamine: 32–34% (w/w),
   water-soluble inert plant matter: 25–51.9% (w/w).

3. A water-soluble complex as set forth in claim 1 wherein the composition of the said extract of *Ginkgo biloba* comprises:
   flavone glycosides: 22 . 45% (w/w),
   ginkgolides 0.1–12% (w/w),
   bilobalide: 0.01–5% (w/w),
   proanthocyanidins: 3–8% (w/w).

4. A water-soluble complex as set forth in claim 3 wherein the amount of said extact in step a), on a dry-weight basis, is equal to about 1.5–3.0 times the weight of the N-methylglucamine.

5. A water-soluble complex as set forth in claim 4 wherein the amount of the said extract in step a), on a dry-weight basis, is about twice the weight of the N-methylglucamine.

* * * * *